(12) United States Patent
Pagedas

(10) Patent No.: US 6,258,102 B1
(45) Date of Patent: *Jul. 10, 2001

(54) REUSABLE LAPROSCOPIC RETRIEVAL MECHANISM

(75) Inventor: Anthony C. Pagedas, Greendale, WI (US)

(73) Assignee: Ancel Surgical R&D, Inc., Greendale, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/461,317

(22) Filed: Dec. 15, 1999

Related U.S. Application Data (63) Continuation-in-part of application No. 09/197,045, filed on Nov. 20, 1998, now Pat. No. 6,059,793.

(51) Int. Cl.[7] .................................................. A61B 12/24
(52) U.S. Cl. ..................................... 606/114; 128/DIG. 24
(58) Field of Search .................................. 606/114, 110; 128/917, DIG. 24

(56) References Cited

U.S. PATENT DOCUMENTS

| | | | |
|---|---|---|---|
| 5,352,184 | * 10/1994 | Goldberg et al. | 606/114 X |
| 5,354,303 | * 10/1994 | Spaeth et al. | 606/114 X |
| 5,368,597 | * 11/1994 | Pagedas | 606/114 |
| 5,779,716 | * 7/1998 | Cano et al. | 606/114 |
| 6,004,330 | 12/1999 | Middleman et al. . | |
| 6,059,793 | * 5/2000 | Pagedas | 606/114 |

* cited by examiner

*Primary Examiner*—Jeffrey A. Smith
(74) *Attorney, Agent, or Firm*—Ryan Kromholz & Manion, S.C.

(57) ABSTRACT

Various embodiments of a reusable surgical device for retrieving a mass during laparoscopic surgery are shown and described. The surgical device has a wand, a rod attached to the wand near the front by a disengaging connector and extending generally parallel to the wand, and a pouch or bag attached to the wand and rod. A portion of the rod is flexible for bowing out from the wand when the rod is pushed forward. The flexible portion straightens to come close to the wand when the rod is pulled backward. The back of the rod may be slidably connected to the wand. A bag suitable for sterilizing may be attached to the rod and wand for receiving a mass during surgery. When the rod bows out, the bag is opened. When the rod straightens, the bag is closed to form a seal. Methods of using the surgical device include attaching a bag, engaging the disengaging connector, and inserting the device through a laparoscopic sleeve for enclosure, manipulation, and retrieval of the mass. Further steps include, removing the surgical device from the body cavity, disengaging the disengaging connector, removing the bag, disposing of the mass, and sterilizing the rod, wand and/or bag.

6 Claims, 9 Drawing Sheets

REUSABLE LAPROSCOPIC RETRIEVAL MECHANISM

RELATED APPLICATION

This is a continuation-in-part application of co-pending U.S. patent application Ser. No. 09/197,045 filed Nov. 20, 1998, now U.S. Pat. No. 6,059,793, and commonly owned by the assignee hereof.

FIELD OF THE INVENTION

This invention relates generally to internal surgery and, more specifically, to a reusable surgical device and methods for accessing and retrieving tissue or other mass from a body cavity.

BACKGROUND OF THE INVENTION

In recent years, the applications for laparoscopic surgery have expanded to include many different procedures. A benefit of laparoscopic operations is the relatively quick recovery period experienced by patients, due to the small incisions that are made in the body. These incisions reduce the trauma and the required healing compared to traditional surgery. Laparoscopic tubes and sleeves with diameters on the order of 10 millimeters are inserted in the body cavity. Various instruments and a video camera are typically directed through laparoscopic sleeves for performing and monitoring the surgical steps.

A particular concern in laparoscopic surgery is the transporting of tissues and other mass that are cut away or retrieved during a surgery. While moving, manipulating, or cutting up a removed mass within the body cavity, pieces of infected or cancerous mass, blood, bile, and other liquids may escape into the body cavity and pose infection problems or other complications. It is desirable to contain these materials in a bag or similar enclosure within the body cavity before removal to minimize the risk of infection or other complications. It is important that the containment of the materials be accomplished as quickly as possible with minimal disturbance to the surgical site.

Instruments with membranes or bags have been designed in an attempt to avoid the complications associated with the removal of tissue during laparoscopic surgery. These devices typically fall into two categories, those that have a bag coiled around an introducing rod that must be unfurled by various maneuvers, and those that pop open a bag using a spring, wire, or other mechanism. A device that falls into the second category is a pouch disclosed in Pagedas (U.S. Pat. No. 5,368,597), which utilizes a flexible rod slidably connected to a wand to create a reclosable pouch. When the rod bows out, the bag is opened. When the rod straightens, the bag is closed to form a seal.

However, the specimen retrieval instruments that are currently on the market, especially the more practical devices, are designed for a single use. Not only does this create a disposal problem, but disposable instruments are not always cost effective. In this era of cost containment, the need often arises for reusable instruments, especially a laparoscopic retrieval pouch that can be sterilized and reused. A second failing of the current specimen retrieval instruments is that they are limited as to the specimen size that can be safely retrieved. A reusable instrument that can employ different size bags and allow rapid removal and replacement of a retrieval pouch would increase surgical efficiency. A third short coming of disposable specimen retrieval instruments is that specimen bags are often ruptured by morcelating instruments or pressure distention against the base of the retrieval bag. A reusable device warrants the additional cost of heavier gauge materials that can withstand the burden of a larger mass, the rigors of morcelation, and the stress of sterilization. U.S. Pat. No. 5,368,597 (Pagedas) is incorporated herein by reference. Although Pagedas (U.S. Pat. No. 5,368,597) alludes to an option where one may slip a sleeve styled bag onto its device, no specific embodiment is given. Moreover, no mention is made of a reusable bag that may be sterilized.

For the foregoing reasons, there is a need for a reusable surgical device, and a method of using such a device, that allows efficient access and retrieval of tissue or other mass from a body cavity.

SUMMARY

According to the present invention, the foregoing and following objects and advantages are achieved by providing a reusable surgical device for safely manipulating and retrieving tissue from a body cavity in operations such as laparascopic surgery, and also a method for using the surgical device. A surgical device having features of the present invention comprises an elongated wand having a front end and a back end, a rod having a flexible portion and a handle portion, and a removable bag. The flexible portion includes a second end attached to the handle portion, and a pivot end near the front end of the wand by a disengaging connector. The handle portion of the rod and the back end of the wand are close to each other so that they can be manipulated from outside a body cavity. Preferably the bag for enclosing and retrieving material during surgery is coupled to the front of the wand and the flexible portion of the rod. The bag may be opened by pushing the rod forward relative to the wand to bow out the flexible portion and may be closed by pulling the rod backward relative to the wand to straighten the flexible portion.

Another object is to provide a surgical device that may be accurately manipulated and controlled with one hand.

Another object is to provide a surgical device that has an adjustable opening that seals when closed.

Another object of the invention is to provide a surgical device that may be sterilized and reused. The reusable portions that can be sterilized may include the wand, the rod, and/or the bag.

Another object of the invention is to provide a surgical device that includes a lock that may be engaged so that a surgeon does not have to hold the device at the desired bag position. Bag positions may include a degree of openness ranging from completely closed to wide open, depending on the extent to which the flexible portion of the rod is bowed.

Another object of the invention is to provide a surgical device that includes a thumb grip to facilitate moving the rod.

Methods of using the surgical device comprise the steps of attaching a bag to the front end of the wand and flexible portion of the rod, engaging the disengaging connector, directing the device into a body cavity, opening the bag by pushing the rod forward to cause the flexible portion to bow out, receiving a mass from the body cavity into the bag, and closing the bag by pulling the rod backwards to cause the flexible portion to straighten and form a seal against the wand. Additional steps may include morcelating the removed mass, removing the surgical device from the body cavity, disengaging the disengaging connector, removing the bag, disposing of the removed mass, and sterilizing the wand, rod and/or bag for reuse.

Accordingly, the present invention provides an economical means for achieving greater efficiency, control and safety in containing materials within, and removing materials from, a body cavity during laparoscopic surgery.

These and other features, aspects and advantages of the present invention will become better understood with regard to the following description. Other objects, advantages and novel features of the invention will become apparent to those skilled in the art. As will be realized, the invention is capable of other and different embodiments and use in other applications, and its several details are capable of modification in various obvious respects, all without departing from the invention. Accordingly, the drawings and descriptions are to be regarded as illustrative in nature and not restrictive.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
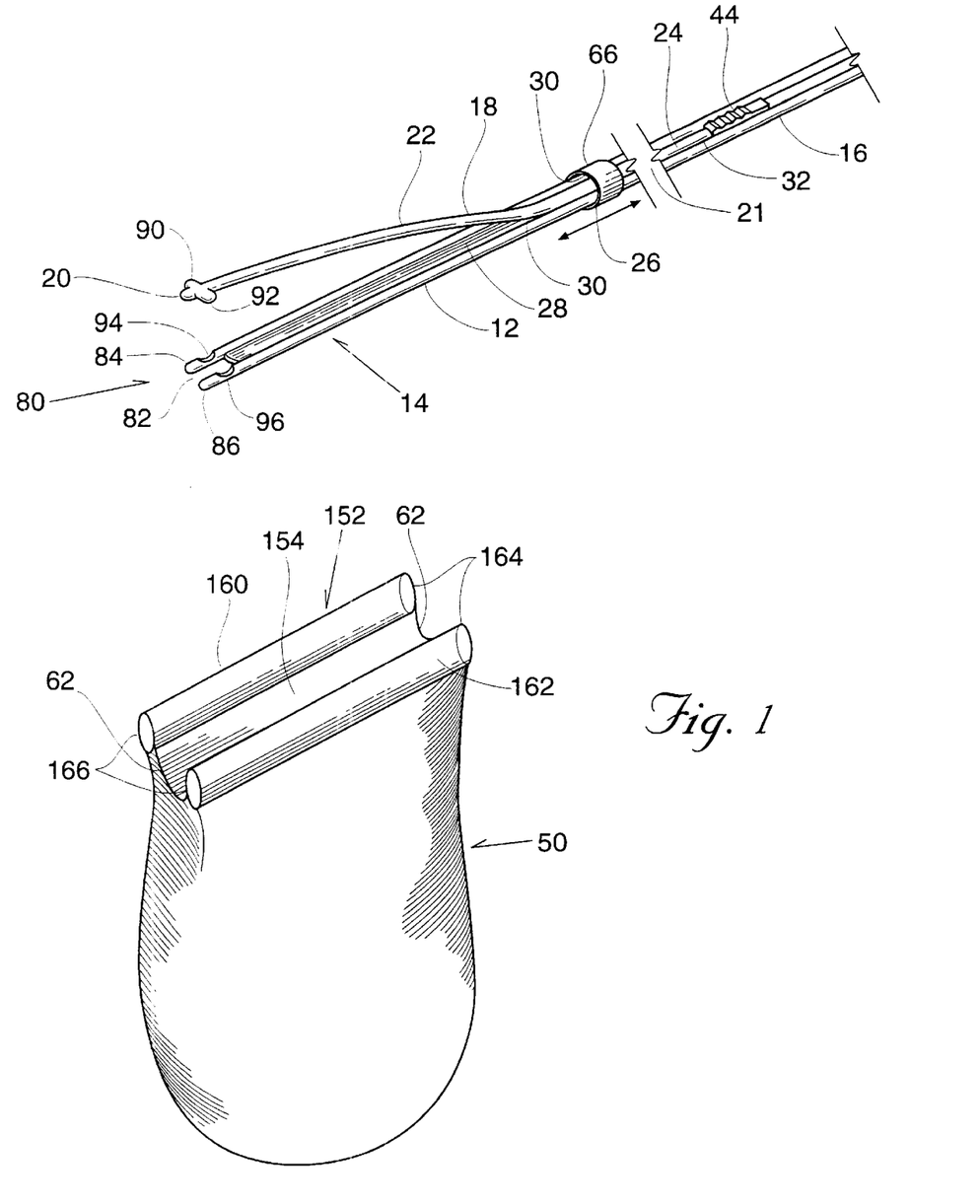
FIG. 1 is a perspective view of one embodiment of the surgical device showing the bag removed from the wand and rod.

As shown in FIG. 1, the preferred embodiment of the surgical device 11 includes an elongated wand 12 with a front end 14 and a back end 16. The wand front end 14 and back end 16 serve as reference points for this discussion, so that "forward" and "front" refer to those movements or locations toward the front end 14 and "backward" and "back" refer to those movements toward the back end 16. The surgical device 11 further includes an elongated rod 18 that has a handle portion 24 connected to a flexible portion 22. The handle portion 24 lies close and generally parallel to the wand 12 and may be coupled to the wand 12 in some fashion. The flexible portion 22 includes a pivot end 20 and a second end 21. The second end 21 of the flexible portion 22 is connected to the handle portion 24, and the pivot end 20 is coupled to the wand's front end 14 using a disengaging connector 80. The surgical device further comprises a removable bag 50 that may be sterilized and reused.

In the preferred embodiment a slot system serves as a connector for holding the handle portion 24 close to the back end 16 of the wand and to set the transition point 26 where the flexible portion 22 transitions from lying close to the wand 12 to bowing out from the wand 12. This transition point 26 may be anywhere on the flexible portion 22 between the pivot end 20 and the second end 21. However, designing a surgical device 11 with the transition point 26 very close to the pivot end 20 would give little longitudinal distance in which the flexible portion could bow. Therefore, the connector preferably extends forward to about the middle of the flexible portion 22.

As shown in FIG. 1, the slot system includes a channel 28 and a lip 32. The channel 28 extends along the longitudinal axis of the wand 12 from the back end 16 and forward preferably to the corresponding location of the rod's pivot end 20. The rod 18 is received in the channel 28. The lip 32 extends partially over the channel 28 for slidably holding the rod 18 in the channel 28 forward up to the location of the front extremity 30. At the front extremity 30, the rod 18 may come out of the channel system as illustrated in FIG. 1.

Figures 5, 5A:
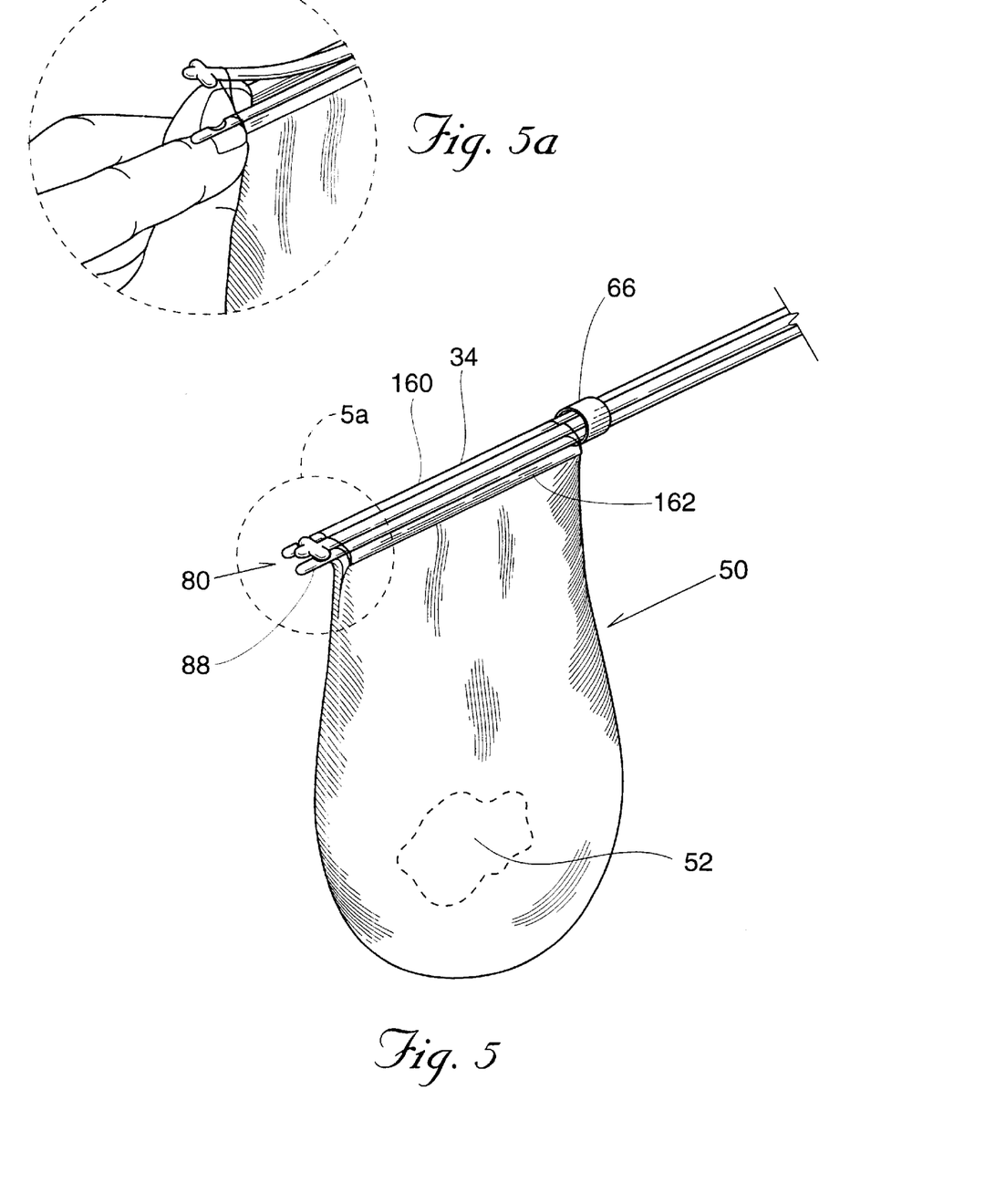
FIG. 5 is a perspective view of one embodiment of the surgical device showing the bag in a closed position.
FIG. 5A shows how one embodiment of the disengaging connector is disengaged.
Figure 6:
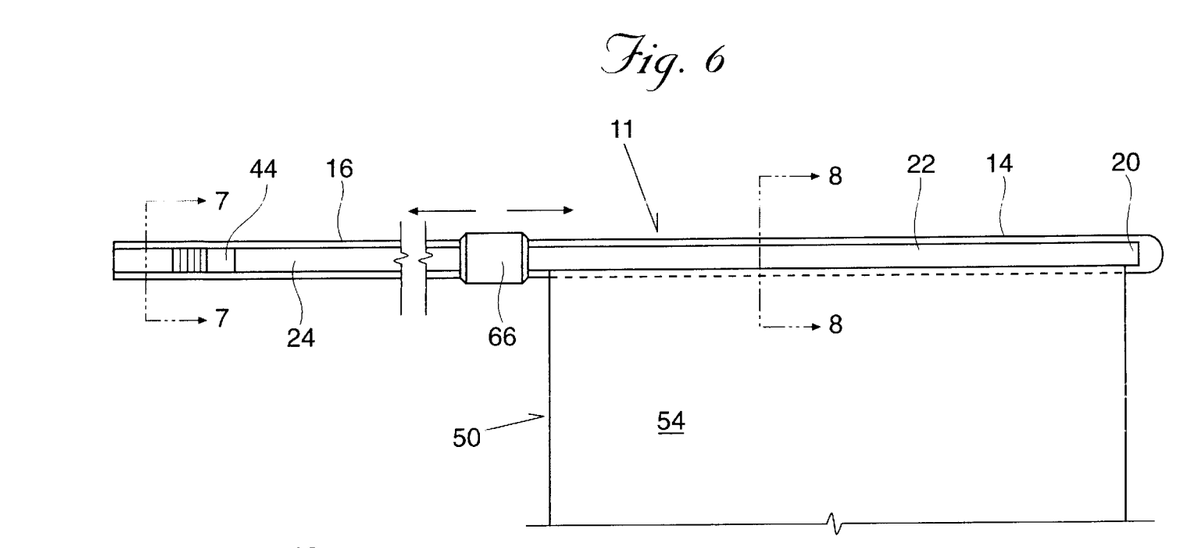
FIG. 6 is a right side elevational view of one embodiment of the invention in a closed position and including an adjustable connector.
Figure 9:
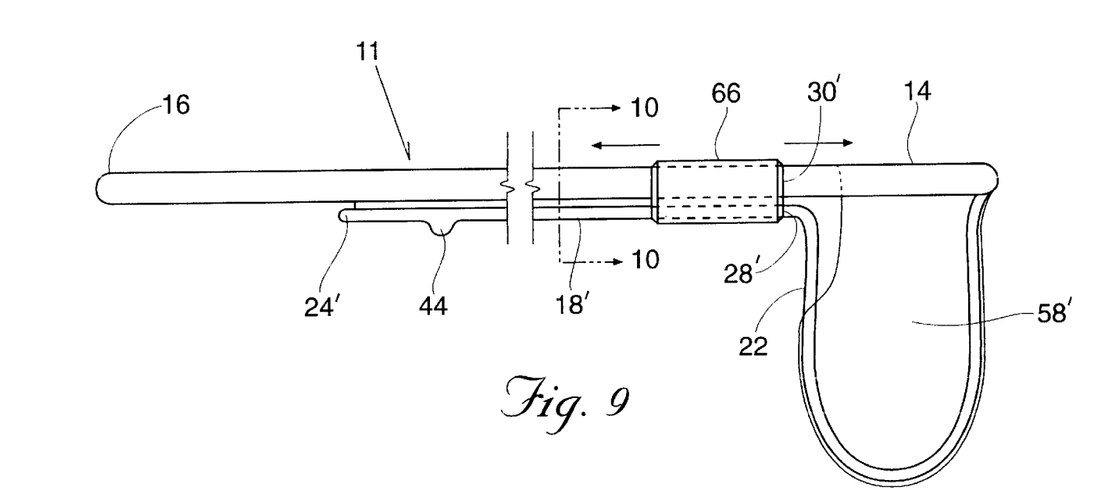
FIG. 9 is a top plan view of another embodiment of the invention with a bag attached and in the open position.
Figure 10:
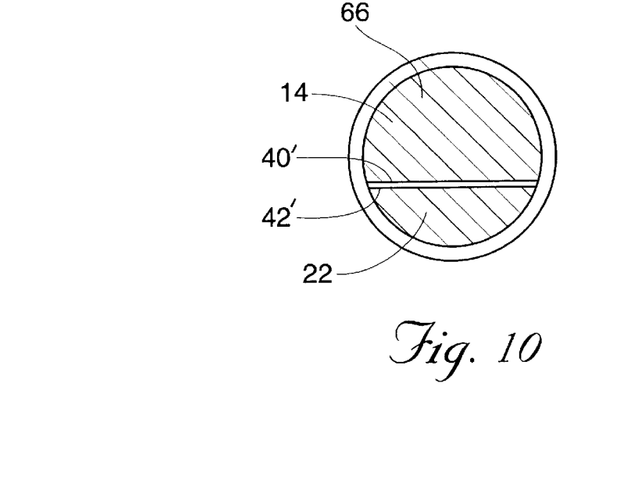
FIG. 10 is a cross-sectional view of one embodiment of the back end of the wand and the handle portion of the rod, taken along line 10—10 in FIG. 9.
Figure 11:
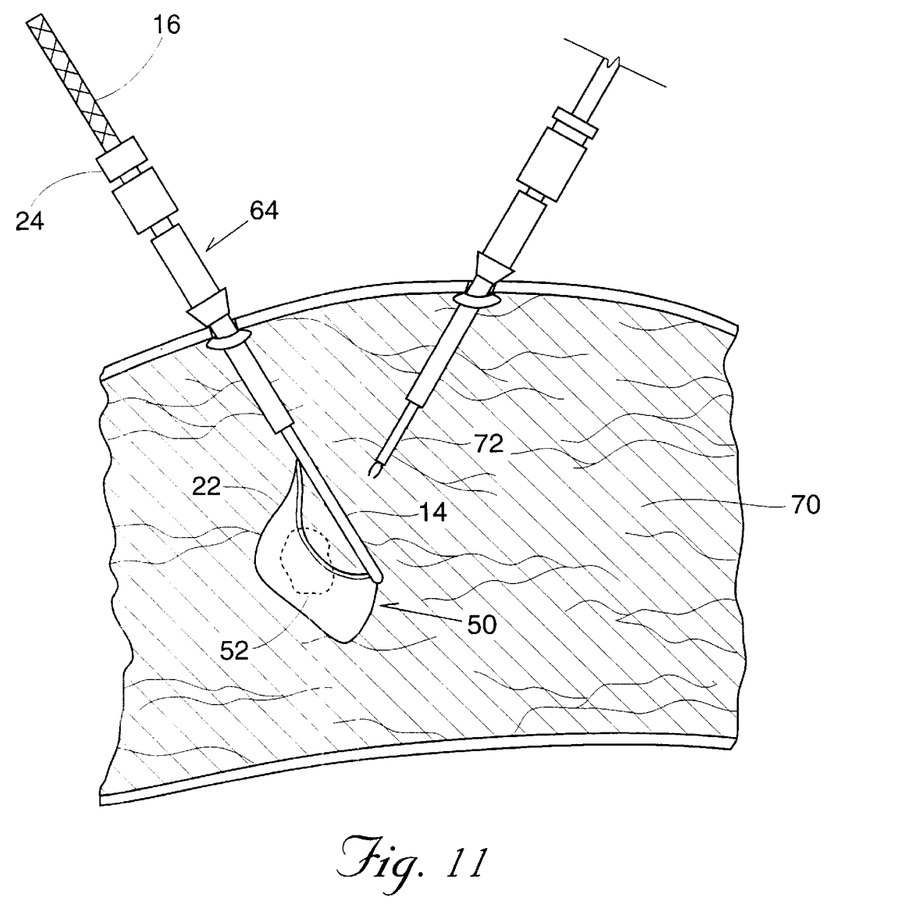
FIG. 11 is a view of one embodiment of the surgical device directed through a laparoscopic sleeve into a body cavity and opened for use in laparoscopic surgery.

As shown in FIG. 6, the channel 28 preferably extends all the way to the location where the pivot end 20 attaches to the front end 14, so that when the flexible portion 22 straightens, it may be received in the channel 28 to form a seal 34 (FIG. 5) between the front end 14 and the flexible portion 22, or between the first portion 160 and the second portion 162 of the bag 50. Other designs may be used to allow the front end 14 and the flexible portion 22 to cooperate to form a seal 34, such as the embodiment in FIGS. 9 and 10 in which the front end 14 and flexible portion 22 inner surfaces 40, 42 are flat.

To bow out the flexible portion 22, the surgeon pushes the handle portion 24 forward, preferably using a thumb grip 44 or some other means that aids comfortable operation. Because it is anchored at the pivot end 20, the rod 18 responds to being pushed by bowing out. To straighten the flexible portion 22 and the bring it closer to the wand 12, the surgeon pulls the handle 24 backwards. Alternatively, the flexible portion 22 may be biased in the closed or unbowed position by allowing the flexible portion 22 to spring back to the unbowed position when pressure on the thumb grip 44 is released.

Regarding the flexibility of the wand 12, there are several options. The wand front end 14 may be rigid in some embodiments and somewhat flexible in other embodiments. For example, the front end 14 may be somewhat flexible for operations in which the surgeon needs to temporarily bend the wand to reach a particular location in the body cavity 70 at a particular angle. However, the wand 12 should be less flexible than the flexible portion 22 of the rod 18, so that the flexible portion 22 bows out from the wand 12 when the handle portion 24 is pushed, rather than the flexible portion 22 and the wand front end 14 bending together in the same direction and thus producing either no opening of the bag 50 or a partial and difficult-to-control opening.

Regarding the flexibility of the rod 18, there are also several options. The flexible portion 22 should be of a flexibility in the outward direction that causes it to bow out relative to the wand 12 when it is pushed. The rod 18 may have a rigid handle portion 24 which may be held close to the wand 12 either by the hand of the person using it or by the laparoscopic sleeve 64. The rod 18 may also be flexible back to and including the handle portion 24, as long as a connector is included to hold and guide the handle portion 24 when it is being pushed and as long as the handle portion 24 flexibility is limited to a range which does not cause buckling and binding of the rod 18 inside the connector. In other words, the rod 18 may have a flexible portion 22 near the pivot end 20 and a relatively rigid handle portion 24, or may be a flexible rod with a flexible portion 22 and a flexible handle portion 24 which cooperates with a connector that holds and guides the handle portion 24.

Figure 7A:
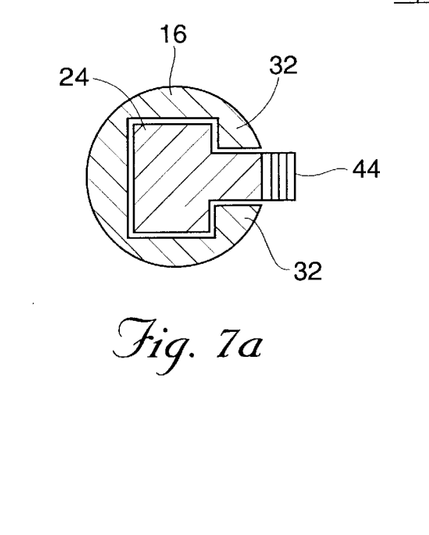
FIG. 7A is a cross-sectional view of one embodiment of the back end of the wand and the handle portion of the rod, taken along line 7—7 in FIG. 6.
Figure 7B:
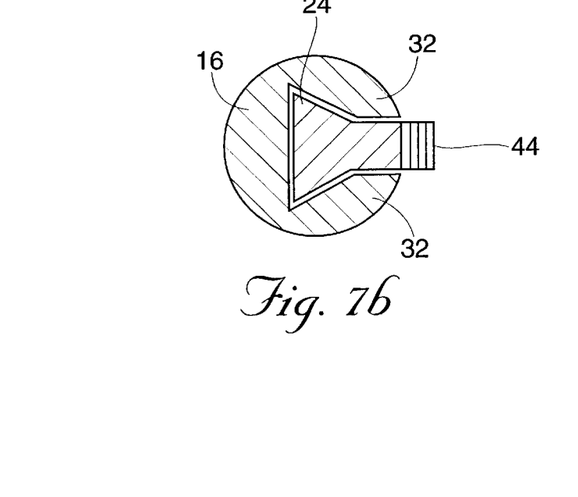
FIG. 7B is a cross-sectional view of one embodiment of the back end of the wand and the handle of the rod, taken along line 7—7 in FIG. 6, illustrating a dovetail-shaped channel system.
Figure 8:
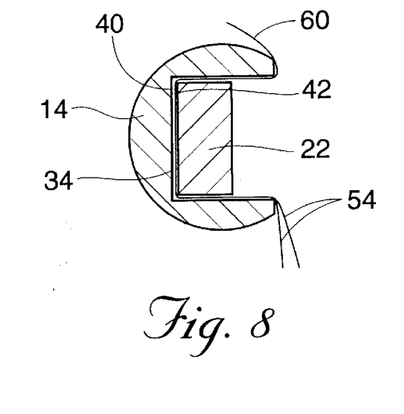
FIG. 8 is a cross sectional view of the front end of the wand and the flexible portion of the rod, taken along line 8—8 in FIG. 6.
Figure 12:
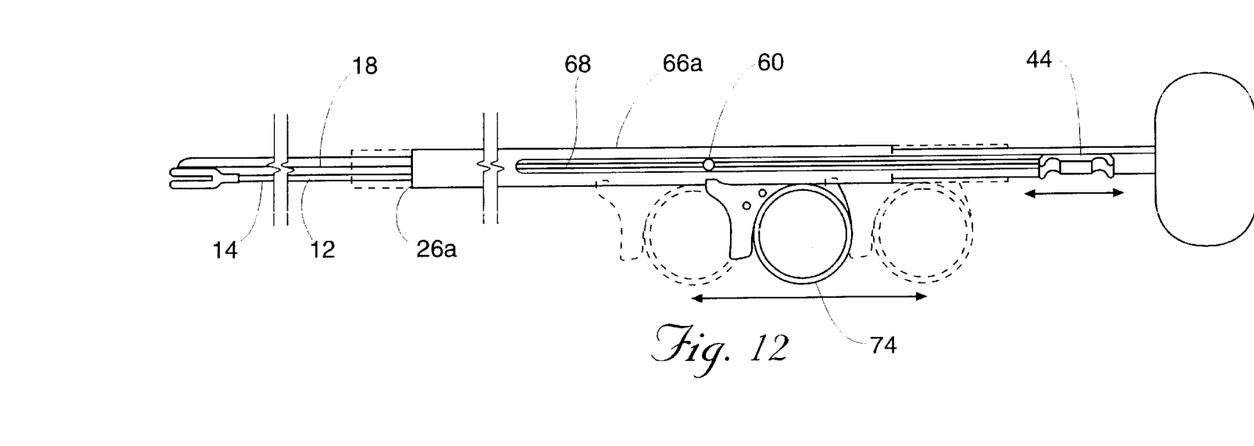
FIG. 12 is a side elevational view of an alternate embodiment of the surgical device and showing a longitudinally extending collar having adjustable locking means.
Figure 13:
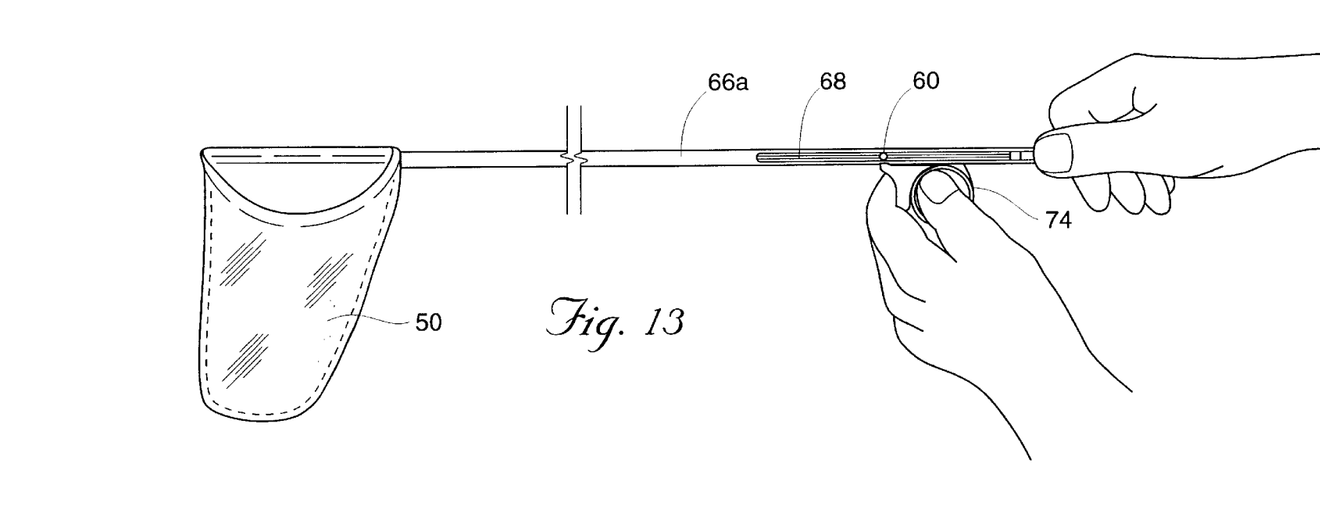
FIG. 13 is a perspective view of an alternate embodiment of the surgical device showing the bag in opened position.

Optionally, embodiments with a rigid handle portion 24 may also include a connector, such as the collar 66 shown in FIGS. 1 and 7, for additional guiding of the handle portion 24. FIG. 1 shows an example of the optional adjustable feature for a connector, the adjustable feature being for changing the longitudinal location of the connector front extremity 30 to change the rod transition point 26. The collar 66 may be moved forward or backward to select a transition point 26 and then may be locked into place, for example with a set screw (not shown), in such a way that the rod 18 may still slide through the collar. An adjustable connector such as the collar 66 may also be added to embodiments having a slot system, as shown in FIG. 6. With reference to FIGS. 12 and 13, an improved embodiment of the invention is depicted. The improvement includes a longitudinally extending collar 66a as illustrated. The collar 66a has a slot 68 substantially coextensive of its length and surrounds both the wand 12 and the rod 18 illustrated in previous figures. The collar 66a may be moved forward or backward to select a transition point 26a and may be locked into place, for example, with a set screw 60. A thumb loop 74 may also be provided for ease in positioning. With an adjustable connector, a surgeon may use a wand 12 and rod 18 with differently-sized bags or bags with differentlyshaped entryways.

The preferred materials for the wand 12 and rod 18 are any materials that fulfill the various flexibility and rigidity requirements while also being safe for sterilization and internal surgery use. Surgical steel could be machined to meet those needs.

Figures 3, 3A:
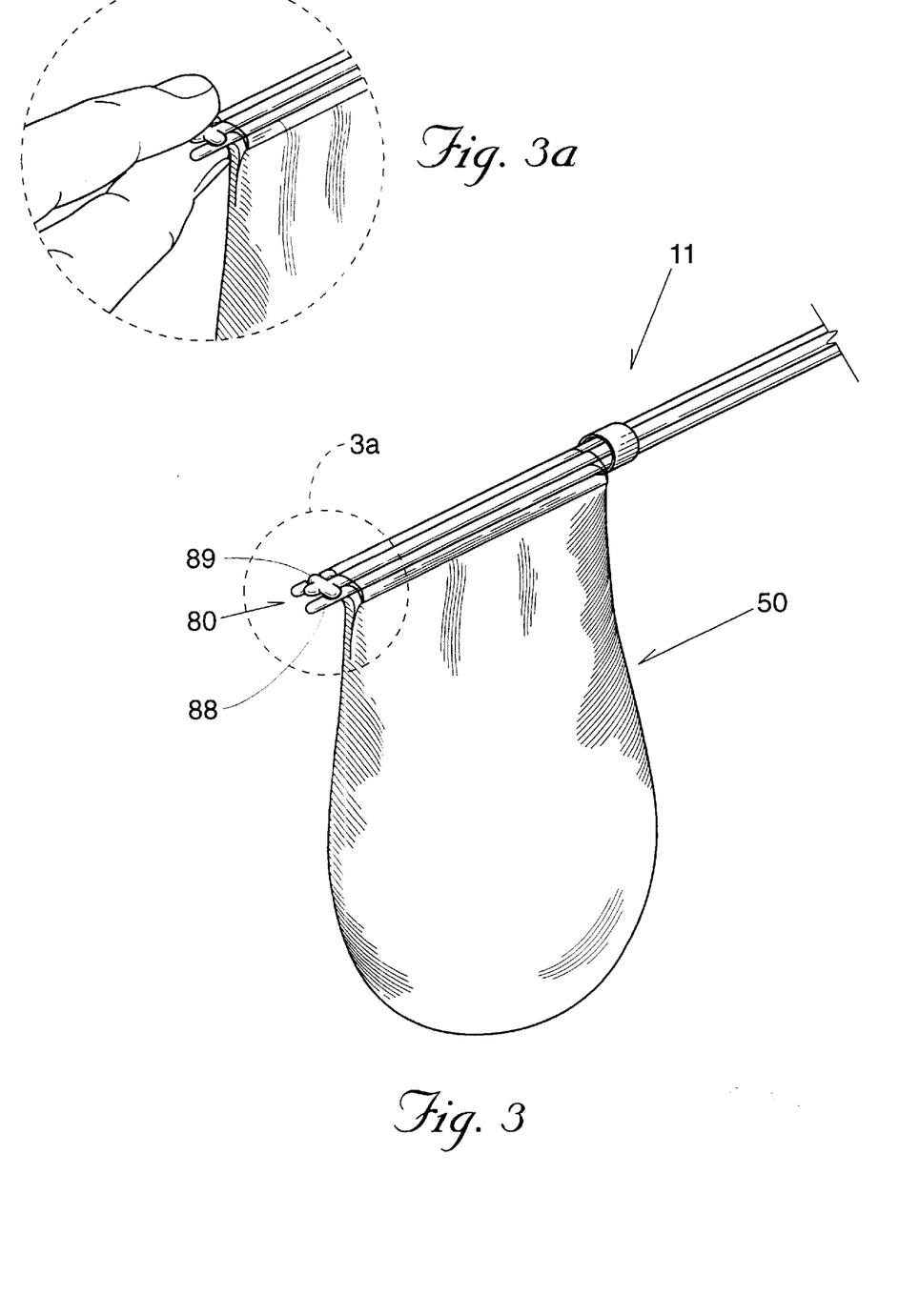
FIG. 3 is a perspective view of one embodiment of the surgical device showing the bag attached to the wand and rod.
FIG. 3A shows how one embodiment of the disengaging connector is engaged.

In the preferred embodiment, the pivot end 20 of the flexible portion 22 is attached to the front end 14 of the wand 12 by a disengaging connector 80. Preferably, the disengaging connector 80 comprises the front end 14 of the wand having a longitudinal slot 82 forming a first prong 84 and a second prong 86. A first notch 94 is formed in the first prong 84, and a second notch 96 is formed in the second prong 86. The flexible portion 22 of the rod 18 includes a first perpendicular spur 90 and an opposing second perpendicular spur 92. As shown in FIG. 3, to engage the disengaging connector 80, the first and second spurs 90, 92 are pressed into the first and second notches 94, 96 respectively. As the handle portion 24 is pushed forward, preferably using a thumb grip 44, and the flexible portion 22 bows out, spurs 90 and 92 rotate in notches 94 and 96, respectively, creating a hinge action. To disengage the connector 80, one pops out the spurs 90, 92 from the notches 94, 96 by applying pressure to the underside 88 of the connector 80 as shown in FIG. 5A.

Although the preferred embodiment includes a disengaging connector 80 with a hinge action, any connector may be used to connect the front end 14 to the pivot end 20 so long as the disengaging connector 80 will not disengage under the stress necessary to bow out the flexible portion 22, yet may be efficiently disengaged to remove the bag 50 for disposal or sterilization. Other such connectors may include a snap, a slot and groove arrangement, other notch and spur configurations, or other comparable cooperating systems.

The preferred embodiment includes a bag 50 for enclosing a mass 52, which may be opened and closed by bowing and straightening action of the flexible portion 22. The bag 50 has a wall 54 for surrounding an interior space 56, and an edge 38 that surrounds the entryway 58. The bag 50 can be disposable or reusable. The preferred materials for the bag 50 should also meet sterility and safety requirements for internal surgery. Transparent plastics, flexible fabrics, and netting could be used. The preferred materials have some memory for tending to stay in a somewhat expanded state rather than tending to collapse, because this feature aids in the quick opening or unwrapping of the bag 50. The preferred materials are impermeable to liquid or are liquid-resistant, for containing infected liquids, but netting or loosely-woven materials could also be of benefit for some surgical procedures. Where morcelating is necessary, a bag 50 may include a fine denier brand fiber that is puncture resistant and able to withstand the cutting of a mass.

Figure 2:
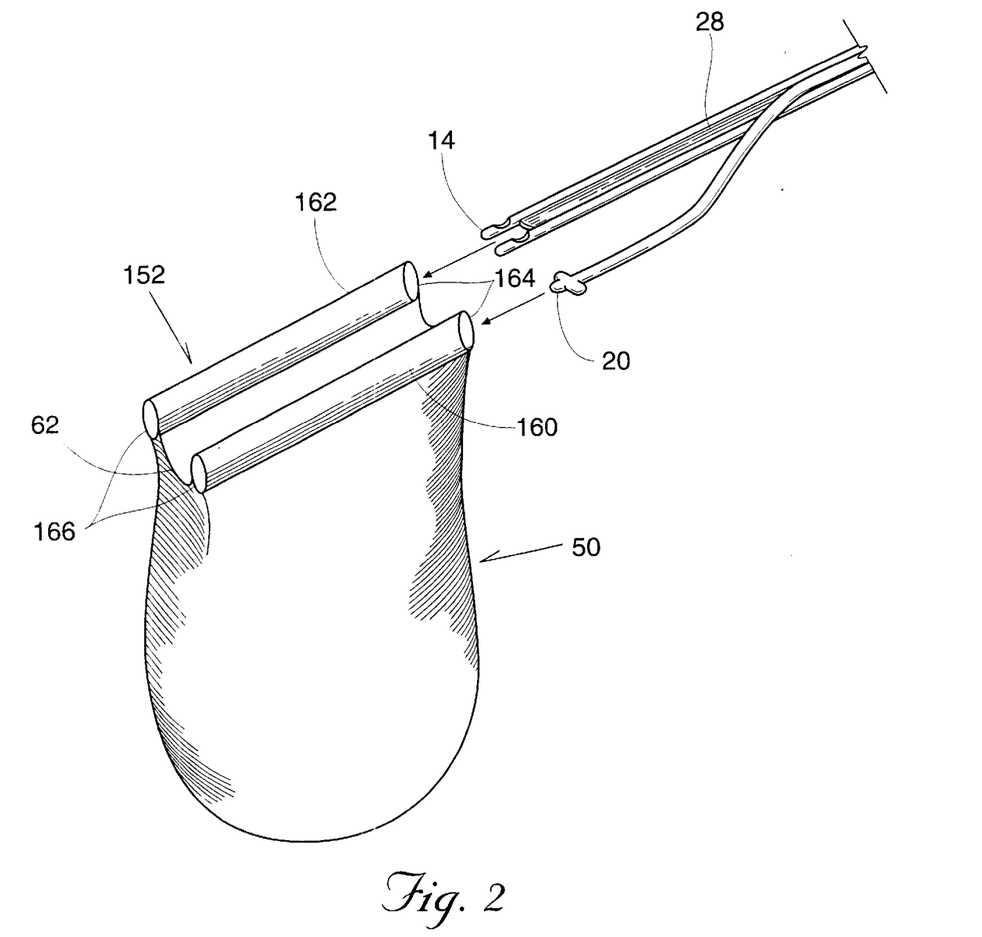
FIG. 2 is a perspective view of one embodiment of the surgical device depicting the bag being attached to the wand and rod.

In one embodiment having a detachable bag 50, the bag 50 includes a sleeved rim 152 with at least one opening 154. In the preferred embodiment, the bag 50 includes a sleeved rim 152 divided into a first part 160 and a second part 162, each part having a first opening 164 and a second opening 166. The first part 160 and second part 162 are divided by an unsupported section 62. The unsupported section 62 allows the flexible portion 22 to slide forward without tearing the bag 50 and to slide backward without pulling the bag 50 underneath the lip 32. As shown in FIG. 2, to attach the bag 50, one slips the flexible portion 22 into the first opening 164 of the first part 160 of the sleeved rim 152, and slips the front end 14 of the wand 12 into the first opening 164 of the second part 162 of the sleeved rim 152. The flexible portion 22 and the front end 14 of the wand 12 slip through the sleeved rim 152 and out the second opening 166 of the sleeved rim 152 at which time the disengaging connector 80 is engaged as shown in FIG. 3 by applying pressure to the underside 88 and topside 89 of the connector 80.

Figure 4:
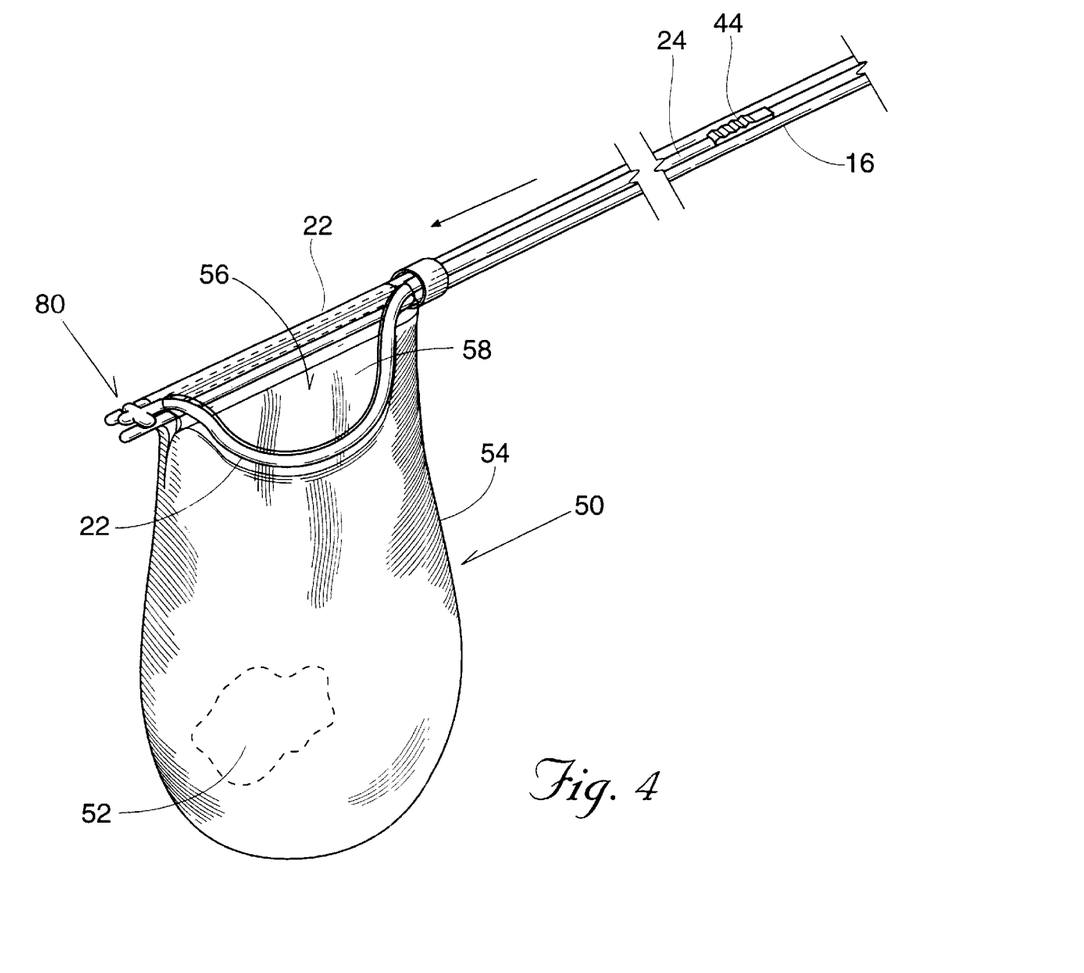
FIG. 4 is a perspective view of one embodiment of the surgical device showing the bag in an opened position.

The method of using the surgical device 11 includes attaching a bag 50 to the front end 14 of the wand 12 and the flexible portion 22 of the rod 18, and directing the surgical device 11 into a body cavity 70, preferably through a laparoscopic sleeve 64, so that the back end 16 and handle portion 24 are accessible by the surgeon. As shown in FIG. 4, the bag 50 is opened by pushing the handle portion 24 forward, preferably using a thumb grip 44. The bag 50 is directed relative to the mass 52 so that the mass 52 moves through the entryway 58 into the interior space 56 of the bag 50. This may be done by moving the bag 50 to the mass 52 and scooping it up or by inserting the mass 52 into the bag 50 with another tool 72. The bag 50 may be closed for further manipulation of the mass 52 or for removal of the surgical device 11 and mass 52 from the body cavity 70. To facilitate removal from the laparoscopic sleeve 64, the bag 50 may be wrapped around the front 14 flexible portion 22 to form a compact and smooth unit.

Optionally, a grinding, cutting, or other surgical tool 72 may be inserted into the interior space 56 of the bag 50 for further manipulation of the mass 52, for example, to cut a large mass into pieces that will fit through the laparoscopic sleeve 64. The surgical tool 72 may be inserted before the bag 50 is closed, or after the bag 50 is closed if the flexible portion 22, front end 14, or bag 50 is adapted to allow a surgical tool 72 to pass through the seal 34. Preferably, the flexible portion 22, front end 14, or bag 50 would also be adapted to maintain a good seal around the inserted surgical tool 72 to prevent escape of mass and liquid. Optionally, a surgical tool 72 could be inserted into the body cavity 70 through the same laparoscopic sleeve 64 as the surgical device 11, or through a hollow passage in the wand 12.

The above described embodiments of this invention are merely descriptive of its principles and are not to be limited. The scope of this invention instead shall be determined from the scope of the following claims, including their equivalents.

In describing the embodiments disclosed herein the inventor has also described all the various alternative structures which are equivalent to one or more elements or limitations of the claimed invention. Beyond what is expressly described herein the inventor has no prior knowledge of any other structures which are equivalent to the invention claimed. Accordingly, the determination of structures, methods, or compositions of matter which are equivalent to the claimed invention shall not be limited to only the alternative structures identified herein, but shall include other structures whether or not they are presently known or unknown.

What is claimed is:

1. A surgical device comprising:
   an elongated wand having a front end and a back end;
   an elongated rod including a handle portion lying generally parallel to said back end of said wand, and a flexible portion having a pivot end and a second end, said second end connected to said handle portion;
   a disengaging connector coupling said front end of said elongated wand to said pivot end of said flexible portion;
   a means of slidably connecting said handle portion to said back end of said wand;
   a bag coupled to said front end and said flexible portion; and
   said means of slidably connecting said handle portion to said back end of said wand comprising a tubular collar surrounding and slidably receiving said wand and said rod, said collar being movable from a first position to a second position relative to said wand, the leading edge of said collar being arranged to be located at a transition point for the second end of said flexible portion.

2. The surgical device of claim 1 further comprising a manually operated thumb loop secured to said tubular collar and arranged for longitudinal movement of said collar in relationship to said elongated rod.

3. A surgical device comprising:
   an elongated wand having a front end and a back end;
   an elongated rod including a handle portion lying generally parallel to said back end of said wand, and a flexible portion having a pivot end and a second end, said second end connected to said handle portion;
   a disengaging connector coupling said front end of said elongated wand to said pivot end of said flexible portion;
   a means of slidably connecting said handle portion to said back end of said wand;
   a bag coupled to said front end and said flexible portion;
   said means of slidably connecting said handle portion to said back end of said wand comprising a tubular collar surrounding and slidably receiving said wand and said rod, said collar being movable from a first position to a second position relative to said wand, the leading edge of said collar being arranged to be located at a transition point for the second end of said flexible portion; and
   wherein said collar includes a longitudinally extending portion and being provided with a longitudinal slot extending along a portion thereof;
   said collar including an adjustable locking means arranged for longitudinal movement of said collar relative to said rod.

4. The surgical device of claim 3 further comprising a manually operated thumb loop secured to said tubular collar and arranged for longitudinal movement of said collar in relationship to said elongated rod.

5. In a surgical device having an elongated wand having a front end and a back end, an elongated rod including a handle portion lying generally parallel to said back end of said wand, and a flexible portion having a pivot end and a second end, said second end connected to said handle portion;
   a disengaging connector coupling said front end of said elongated wand to said pivot end of said flexible portion;
   a means of slidably connecting said handle portion to said back end of said wand;
   a bag coupled to said front end and said flexible portion;
   the improvement comprising:
   a tubular collar surrounding and slidably receiving said wand and said rod, said collar being movable from a first position to a second position relative to said wand, the leading edge of said collar being arranged to be located at a transition point for the second end of said flexible portion.

6. In a surgical device having an elongated wand having a front end and a back end, an elongated rod including a handle portion lying generally parallel to said back end of said wand, and a flexible portion having a pivot end and a second end, said second end connected to said handle portion;
   a disengaging connector coupling said front end of said elongated wand to said pivot end of said flexible portion;
   a means of slidably connecting said handle portion to said back end of said wand;
   a bag coupled to said front end and said flexible portion;
   a tubular collar surrounding and slidably receiving said wand and said rod, said collar being movable from a first position to a second position relative to said wand, the leading edge of said collar being arranged to be located at a transition point for the second end of said flexible portion, the improvement comprising;

said collar including a longitudinally extending portion and being provided with a longitudinal slot extending along a portion thereof; and said collar including an adjustable locking means arranged for longitudinal movement of said collar relative to said rod.

* * * * *

UNITED STATES PATENT AND TRADEMARK OFFICE
CERTIFICATE OF CORRECTION

PATENT NO. : 6,258,102 B1
DATED : July 10, 2001
INVENTOR(S) : Anthony C. Pagedas It is certified that error appears in the above-identified patent and that said Letters Patent is hereby corrected as shown below:

<u>Title page,</u>
Item [54], please delete all reference to the title "REUSABLE LAPROSCOPIC RETRIEVAL MECHANISM" and substitute therefore -- REUSABLE LAPAROSCOPIC RETRIEVAL MECHANISM --.

Signed and Sealed this

Twenty-ninth Day of January, 2002

Attest:

JAMES E. ROGAN
*Director of the United States Patent and Trademark Office*

*Attesting Officer*